United States Patent [19]

Krstenansky

[11] Patent Number: 5,232,912
[45] Date of Patent: Aug. 3, 1993

[54] ANTICOAGULANT PEPTIDES

[75] Inventor: John L. Krstenansky, Mountain View, Calif.

[73] Assignee: Merrell Dow Pharmaceuticals Inc., Cincinnati, Ohio

[21] Appl. No.: 970,596

[22] Filed: Oct. 30, 1992

Related U.S. Application Data

[63] Continuation of Ser. No. 645,539, Jan. 24, 1991, abandoned, which is a continuation-in-part of Ser. No. 281,121, Dec. 7, 1988, abandoned.

[51] Int. Cl.$^5$ .................. A61K 37/00; C07K 5/00
[52] U.S. Cl. ...................... 514/15; 514/822; 530/328; 930/20; 930/21
[58] Field of Search ............... 530/327, 328; 514/15, 514/822; 930/20, 21

[56] References Cited

FOREIGN PATENT DOCUMENTS 0276014 7/1988 European Pat. Off. .

OTHER PUBLICATIONS

Krstenansky et al. Thromb. Haem. vol. 63(2) 208–214 (1990).
Krstenansky et al. Thromb. Res. vol. 54, 319–325 (1989).
Krstenansky et al. J. Med. Chem. vol. 30, 1688–1691 (1987).

Primary Examiner—Merrell C. Cashion, Jr.
Assistant Examiner—B. Celsa
Attorney, Agent, or Firm—Kenneth J. Collier

[57] ABSTRACT

This invention relates to peptide derivatives which are useful anticoagulant agents.

10 Claims, No Drawings

SEQUENCE LISTING (1) GENERAL INFORMATION:
    (i) APPLICANT: Krstenansky, John L
    (ii) TITLE OF INVENTION: Anticoagulant Peptides
    (iii) NUMBER OF SEQUENCES: 9
    (iv) CORRESPONDENCE ADDRESS:
        (A) ADDRESSEE: Marion Merrell Dow Inc.
        (B) STREET: 2110 East Galbraith Rd.
        (C) CITY: Cincinnati P.O. Box 156300
        (D) STATE: Ohio
        (E) COUNTRY: USA
        (F) ZIP: 45215-6300
    (v) COMPUTER READABLE FORM:
        (A) MEDIUM TYPE: Floppy disk
        (B) COMPUTER: IBM PC compatible
        (C) OPERATING SYSTEM: PC-DOS/MS-DOS
        (D) SOFTWARE: PatentIn Release #1.0, Version #1.25
    (vi) CURRENT APPLICATION DATA:
        (A) APPLICATION NUMBER: US 07/645,539
        (B) FILING DATE: 24-JAN-1991
        (C) CLASSIFICATION:
    (viii) ATTORNEY/AGENT INFORMATION:
        (A) NAME: Collier, Kenneth J
        (B) REGISTRATION NUMBER: P-34,982
        (C) REFERENCE/DOCKET NUMBER: M01384A
    (ix) TELECOMMUNICATION INFORMATION:
        (A) TELEPHONE: (513) 948-7834
        (B) TELEFAX: (513) 948-7961
        (C) TELEX: 214320

(2) INFORMATION FOR SEQ ID NO:1:
    (i) SEQUENCE CHARACTERISTICS:
        (A) LENGTH: 65 amino acids
        (B) TYPE: amino acid
        (D) TOPOLOGY: linear
    (ii) MOLECULE TYPE: peptide
    (vi) ORIGINAL SOURCE:
        (A) ORGANISM: *Hirudo medicinalis* (Medicinal Leech)
        (B) STRAIN: Class: Eukaryota; Metazoa; Annelida; Hirudinea
    (ix) FEATURE:
        (A) NAME/KEY: Peptide
        (B) LOCATION: 1..65
        (D) OTHER INFORMATION: /label = Features
            /note = "Serine Protease Inhibitor; Sulfatation;
            Multigene Family; 3D-Structure; 6970 MN; 20445
            CN."
    (ix) FEATURE:
        (A) NAME/KEY: Peptide
        (B) LOCATION: 1..65
        (D) OTHER INFORMATION: /label = Properties
            /note = "Hirudin is a potent thrombin-specific
            protease inhibitor that forms a stable
            non-covalent complex with"
    (ix) FEATURE:
        (A) NAME/KEY: Peptide
        (B) LOCATION: 1..65
        (D) OTHER INFORMATION: /label = Features
            /note = "(cont'd) alpha-thrombin, thereby
            abolishing its ability to cleave fibrinogen."
    (ix) FEATURE:
        (A) NAME/KEY: Peptide
        (B) LOCATION: 63
        (D) OTHER INFORMATION: /label = Features
            /note = "Modified Residue (RES), RES 63 Sulfatation"
    (x) PUBLICATION INFORMATION:
        (A) AUTHORS:   Dodt, J
                          Muller, H P
                          Seemuller, U -continued

SEQUENCE LISTING

Chang, J Y
   (C) JOURNAL: FEBS Lett.
   (E) ISSUE: 165
   (F) PAGES: 180-183
   (G) DATE: 1984
 (x) PUBLICATION INFORMATION:
   (A) AUTHORS: Petersen, T E
        Roberts, H R
        Sottrup-Jensen, L
        Magnusson, S
        Bagdy, D
   (C) JOURNAL: Book: Protides of The Biological Fluids, Proc.
     23rd Colloq.
   (F) PAGES: 145-149
   (G) DATE: 1976
 (x) PUBLICATION INFORMATION:
   (A) AUTHORS: Folkers M, P J
        Clore, G M
        Driscoll, P C
        Dodt, J
        Koehler, S
   (B) TITLE: Structure by NMR
   (C) JOURNAL: Abstracted in GenBank
 (xi) SEQUENCE DESCRIPTION: SEQ ID NO:1:

Val Val Tyr Thr Asp Cys Thr Glu Ser Gly Gln Asn Leu Cys Leu Cys
1             5                     10                    15

Glu Gly Ser Asn Val Cys Gly Gln Gly Asn Lys Cys Ile Leu Gly Ser
            20                  25                  30

Asp Gly Glu Lys Asn Gln Cys Val Thr Gly Glu Gly Thr Pro Lys Pro
        35              40                      45

Gln Ser His Asn Asp Gly Asp Phe Glu Glu Ile Pro Glu Glu Tyr Leu
    50              55                      60

Gln
65

(2) INFORMATION FOR SEQ ID NO:2:
 (i) SEQUENCE CHARACTERISTICS:
   (A) LENGTH: 66 amino acids
   (B) TYPE: amino acid
   (D) TOPOLOGY: linear
 (ii) MOLECULE TYPE: peptide
 (vi) ORIGINAL SOURCE:
   (A) ORGANISM: *Hirudo medicinalis* (Medicinal Leech)
   (B) STRAIN: Eukaryota; Metazoa; Annelida; Hirudinea
 (ix) FEATURE:
   (A) NAME/KEY: Peptide
   (B) LOCATION: 1..66
   (D) OTHER INFORMATION: /label = Features
     /note = "Serine protease inhibitor; multigene
     family; 7026 MW; 20620 CN."
 (ix) FEATURE:
   (A) NAME/KEY: Peptide
   (B) LOCATION: 64
   (D) OTHER INFORMATION: /label = Features
     /note = "Modified Residue (RES), RES 64
     Sulfatation"
 (ix) FEATURE:
   (A) NAME/KEY: Peptide
   (B) LOCATION: 1..66
   (D) OTHER INFORMATION: /label = Properties
     /note = "Hirudin is a potent thrombin-specific
     protease inhibitor that forms a stable
     non-covalent complex with alpha-thrombin,"
 (ix) FEATURE:
   (A) NAME/KEY: Peptide
   (B) LOCATION: 1..66
   (D) OTHER INFORMATION: /label = Properties
     /note = "(cont'd) thereby abolishing its ability to
     cleave fibrinogen"
 (x) PUBLICATION INFORMATION:
   (A) AUTHORS: Dodt, J
        Machleidt, W
        Seemuller, U
        Maschler, R
        Fritz, H
   (C) JOURNAL: Biol. Chem. Hoppe-Seyler
   (D) VOLUME: 367

-continued

| SEQUENCE LISTING |
|---|

(F) PAGES: 803-811
(G) DATE: 1986
(xi) SEQUENCE DESCRIPTION: SEQ ID NO:2:

| Ile 1 | Thr | Tyr | Thr | Asp 5 | Cys | Thr | Glu | Ser | Gly 10 | Gln | Asn | Leu | Cys | Leu 15 | Cys |
|---|---|---|---|---|---|---|---|---|---|---|---|---|---|---|---|
| Glu | Gly | Ser | Asn 20 | Val | Cys | Gly | Lys | Gly 25 | Asn | Lys | Cys | Ile | Leu 30 | Gly | Ser |
| Gln | Gly | Lys 35 | Asp | Asn | Gln | Cys | Val 40 | Thr | Gly | Glu | Gly | Thr 45 | Pro | Lys | Pro |
| Gln | Ser 50 | His | Asn | Gln | Gly | Asp 55 | Phe | Glu | Pro | Ile | Pro 60 | Glu | Asp | Ala | Tyr |
| Asp 65 | Glu | | | | | | | | | | | | | | |

(2) INFORMATION FOR SEQ ID NO:3:
    (i) SEQUENCE CHARACTERISTICS:
        (A) LENGTH: 72 amino acids
        (B) TYPE: amino acid
        (D) TOPOLOGY: linear
    (ii) MOLECULE TYPE: peptide
    (vi) ORIGINAL SOURCE:
        (A) ORGANISM: *Hirudo medicinalis* (Medicinal Leech)
        (B) STRAIN: Eukaryota; Metazoa; Annelida; Hirudinea
    (ix) FEATURE:
        (A) NAME/KEY: Peptide
        (B) LOCATION: 1..72
        (D) OTHER INFORMATION: /label = Features
            /note = "Serine protease inhibitor; sulfatation;
            multigene family; 7571 MW; 24730 CN."
    (ix) FEATURE:
        (A) NAME/KEY: Domain
        (B) LOCATION: 1..7
        (D) OTHER INFORMATION: /label = Features
            /note = "Signal Sequence"
    (ix) FEATURE:
        (A) NAME/KEY: Peptide
        (B) LOCATION: 8..72
        (D) OTHER INFORMATION: /label = Features
            /note = "Mature Hirudin"
    (ix) FEATURE:
        (A) NAME/KEY: Peptide
        (B) LOCATION: 1..72
        (D) OTHER INFORMATION: /label = Properties
            /note = "Hirudin is a potent thrombin-specific
            protease inhibitor that forms a stable
            non-covalent complex with alpha-thrombin"
    (ix) FEATURE:
        (A) NAME/KEY: Peptide
        (B) LOCATION: 1..72
        (D) OTHER INFORMATION: /label = Properties
            /note = "(cont'd) thereby abolishing its ability to
            cleave fibrinogen."
    (ix) FEATURE:
        (A) NAME/KEY: Peptide
        (B) LOCATION: 1..72
        (D) OTHER INFORMATION: /label = Features
            /note = "Modified Res (RES), RES (RES) Sulfatation"
    (xi) SEQUENCE DESCRIPTION: SEQ ID NO:3:

| Ala 1 | Ile | Cys | Val | Ser 5 | Gln | Ala | Ile | Thr | Tyr 10 | Thr | Asp | Cys | Thr | Glu 15 | Ser |
|---|---|---|---|---|---|---|---|---|---|---|---|---|---|---|---|
| Gly | Gln | Asn | Leu 20 | Cys | Leu | Cys | Glu | Gly 25 | Ser | Asn | Val | Cys | Gly 30 | Lys | Gly |
| Asn | Lys | Cys 35 | Ile | Leu | Gly | Ser | Asn 40 | Gly | Lys | Gly | Asn | Gln 45 | Cys | Val | Thr |
| Gly | Glu 50 | Gly | Thr | Pro | Asn | Pro 55 | Glu | Ser | His | Asn | Asn 60 | Gly | Asp | Phe | Glu |
| Glu 65 | Ile | Pro | Glu | Glu | Tyr 70 | Leu | Gln | | | | | | | | |

(2) INFORMATION FOR SEQ ID NO:4:
    (i) SEQUENCE CHARACTERISTICS:
        (A) LENGTH: 10 amino acids
        (B) TYPE: amino acid

SEQUENCE LISTING (D) TOPOLOGY: linear
 (ii) MOLECULE TYPE: peptide
 (ix) FEATURE:
   (A) NAME/KEY: Peptide
   (B) LOCATION: 1..10
   (D) OTHER INFORMATION: /label = Features
    /note = "Serine protease inhibitor; carboxy
    terminus of Hirudin"
 (ix) FEATURE:
   (A) NAME/KEY: Peptide
   (B) LOCATION: 1
   (D) OTHER INFORMATION: /label = Features
    /note = "Xaa = N-alpha-succinyl-tyrosine (Suc—Tyr)"
 (ix) FEATURE:
   (A) NAME/KEY: Peptide
   (B) LOCATION: 5
   (D) OTHER INFORMATION: /label = Features
    /note = "Xaa = L-2-pipecolic acid (Pip)"
 (ix) FEATURE:
   (A) NAME/KEY: Peptide
   (B) LOCATION: 9
   (D) OTHER INFORMATION: /label = Features
    /note = "Xaa = cyclohexylalanine (Cha)"
 (ix) FEATURE:
   (A) NAME/KEY: Peptide
   (B) LOCATION: 10
   (D) OTHER INFORMATION: /label = Features
    /note = "Xaa = D-glutamic acid (D-Glu)"
 (ix) FEATURE:
   (A) NAME/KEY: Peptide
   (B) LOCATION: 1..10
   (D) OTHER INFORMATION: /label = Properties
    /note = "Hirudin peptide is a potent
    thrombin-specific protease inhibitor that forms a
    stable non-covalent complex with"
 (ix) FEATURE:
   (A) NAME/KEY: Peptide
   (B) LOCATION: 1..10
   (D) OTHER INFORMATION: /label = Properties
    /note = "(cont'd) alpha-thrombin. Unlike other
    thrombin inhibitors, said peptide does not occupy
    the catalytic site of"
 (ix) FEATURE:
   (A) NAME/KEY: Peptide
   (B) LOCATION: 1..10
   (D) OTHER INFORMATION: /label = Properties
    /note = "(cont'd) alpha-thrombin to inhibit
    cleavage of fibinogen."
 (xi) SEQUENCE DESCRIPTION: SEQ ID NO:4:

Xaa Glu Pro Ile Xaa Glu Glu Ala Xaa Xaa
1          5             10

(2) INFORMATION FOR SEQ ID NO:5:
 (i) SEQUENCE CHARACTERISTICS:
   (A) LENGTH: 10 amino acids
   (B) TYPE: amino acid
   (D) TOPOLOGY: linear
 (ii) MOLECULE TYPE: peptide
 (ix) FEATURE:
   (A) NAME/KEY: Peptide
   (B) LOCATION: 1..10
   (D) OTHER INFORMATION: /label = Features
    /note = "Serine protease inhibitor; carboxy
    terminus of Hirudin"
 (ix) FEATURE:
   (A) NAME/KEY: Peptide
   (B) LOCATION: 1
   (D) OTHER INFORMATION: /label = Features
    /note = "Xaa = N-alpha-succinyl-tyrosine (Suc—Tyr)"
 (ix) FEATURE:
   (A) NAME/KEY: Peptide
   (B) LOCATION: 3
   (D) OTHER INFORMATION: /label = Features
    /note = "Xaa = L-2-Pipecolic acid (Pip)"
 (ix) FEATURE:
   (A) NAME/KEY: Peptide
   (B) LOCATION: 9
   (D) OTHER INFORMATION: /label = Features
    /note = "Xaa = Cyclohexylalanine (Cha)"
 (ix) FEATURE:
   (A) NAME/KEY: Peptide

-continued
SEQUENCE LISTING (B) LOCATION: 10
                (D) OTHER INFORMATION: /label = Features
                    /note = "Xaa = D-glutamic acid (D-Glu)"
        (ix) FEATURE:
                (A) NAME/KEY: Peptide
                (B) LOCATION: 1..10
                (D) OTHER INFORMATION: /label = Properties
                    /note = "Hirudin peptide is a potent
                    thrombin-specific protease inhibitor that forms a
                    stable non-covalent complex with"
        (ix) FEATURE:
                (A) NAME/KEY: Peptide
                (B) LOCATION: 1..10
                (D) OTHER INFORMATION: /label = Properties
                    /note = "(cont'd) alpha-thrombin. Unlike other
                    thrombin inhibitors, said peptide does not occupy
                    the catalytic site of"
        (ix) FEATURE:
                (A) NAME/KEY: Peptide
                (B) LOCATION: 1..10
                (D) OTHER INFORMATION: /label = Properties
                    /note = "(cont'd) alpha-thrombin to inhibit
                    cleavage of fibinogen."
        (xi) SEQUENCE DESCRIPTION: SEQ ID NO:5:
Xaa  Glu  Xaa  Ile  Pro  Glu  Glu  Ala  Xaa  Xaa
1                   5                        10

(2) INFORMATION FOR SEQ ID NO:6:
        (i) SEQUENCE CHARACTERISTICS:
                (A) LENGTH: 10 amino acids
                (B) TYPE: amino acid
                (D) TOPOLOGY: linear
        (ii) MOLECULE TYPE: peptide
        (ix) FEATURE:
                (A) NAME/KEY: Peptide
                (B) LOCATION: 1..10
                (D) OTHER INFORMATION: /label = Features
                    /note = "Serine protease inhibitor; carboxy
                    terminus of Hirudin."
        (ix) FEATURE:
                (A) NAME/KEY: Peptide
                (B) LOCATION: 1
                (D) OTHER INFORMATION: /label = Features
                    /note = "Xaa = N-alpha-succinyl-tyrosine (Suc—Tyr)"
        (ix) FEATURE:
                (A) NAME/KEY: Peptide
                (B) LOCATION: 5
                (D) OTHER INFORMATION: /label = Features
                    /note = "Xaa = L-azetidine-2-carboxylate (Azd)"
        (ix) FEATURE:
                (A) NAME/KEY: Peptide
                (B) LOCATION: 9
                (D) OTHER INFORMATION: /label = Features
                    /note = "Xaa = Cyclohexylalanine (Cha)"
        (ix) FEATURE:
                (A) NAME/KEY: Peptide
                (B) LOCATION: 10
                (D) OTHER INFORMATION: /label = Features
                    /note = "Xaa = D-glutamic acid (D-Glu)"
        (ix) FEATURE:
                (A) NAME/KEY: Peptide
                (B) LOCATION: 1..10
                (D) OTHER INFORMATION: /label = Properties
                    /note = "Hirudin peptide is a potent
                    thrombin-specific protease inhibitor that forms a
                    stable non-covalent complex"
        (ix) FEATURE:
                (A) NAME/KEY: Peptide
                (B) LOCATION: 1..10
                (D) OTHER INFORMATION: /label = Properties
                    /note = "(cont'd) with alpha-thrombin. Unlike
                    other thrombin inhibitors, said peptide does not
                    occupy the catalytic site
        (ix) FEATURE:
                (A) NAME/KEY: Peptide
                (B) LOCATION: 1..10
                (D) OTHER INFORMATION: /label = Properties
                    /note = "(cont'd) of alpha-thrombin to inhibit
                    cleavage of fibinogen."
        (xi) SEQUENCE DESCRIPTION: SEQ ID NO:6:
Xaa  Glu  Pro  Ile  Xaa  Glu  Glu  Ala  Xaa  Xaa -continued

SEQUENCE LISTING

| 1 | 5 | 10 |

(2) INFORMATION FOR SEQ ID NO:7:
    (i) SEQUENCE CHARACTERISTICS:
        (A) LENGTH: 10 amino acids
        (B) TYPE: amino acid
        (D) TOPOLOGY: linear
    (ii) MOLECULE TYPE: peptide
    (ix) FEATURE:
        (A) NAME/KEY: Peptide
        (B) LOCATION: 1..10
        (D) OTHER INFORMATION: /label = Features
            /note = "Serine protease inhibitor; carboxy
            terminus of Hirudin."
    (ix) FEATURE:
        (A) NAME/KEY: Peptide
        (B) LOCATION: 1
        (D) OTHER INFORMATION: /label = Features
            /note = "Xaa = N-alpha-succinyl-tyrosine (Suc—Tyr)"
    (ix) FEATURE:
        (A) NAME/KEY: Peptide
        (B) LOCATION: 3
        (D) OTHER INFORMATION: /label = Features
            /note = "Xaa = L-Azetidine-2-Carboxylate (Azd)"
    (ix) FEATURE:
        (A) NAME/KEY: Peptide
        (B) LOCATION: 9
        (D) OTHER INFORMATION: /label = Features
            /note = "Xaa = Cyclohexylalanine (Cha)"
    (ix) FEATURE:
        (A) NAME/KEY: Peptide
        (B) LOCATION: 10
        (D) OTHER INFORMATION: /label = Features
            /note = "Xaa = D-glutamic acid (D-Glu)"
    (ix) FEATURE:
        (A) NAME/KEY: Peptide
        (B) LOCATION: 1..10
        (D) OTHER INFORMATION: /label = Properties
            /note = "Hirudin peptide is a potent
            thrombin-specific protease inhibitor that forms a
            stable non-covalent complex with"
    (ix) FEATURE:
        (A) NAME/KEY: Peptide
        (B) LOCATION: 1..10
        (D) OTHER INFORMATION: /label = Properties
            /note = "(cont'd) alpha-thrombin. Unlike other
            thrombin inhibitors, said peptide does not occupy
            the catalytic site of"
    (ix) FEATURE:
        (A) NAME/KEY: Peptide
        (B) LOCATION: 1..10
        (D) OTHER INFORMATION: /label = Properties
            /note = "(cont'd) alpha-thrombin to inhibit
            cleavage of fibrinogen."
    (xi) SEQUENCE DESCRIPTION: SEQ ID NO:7:

Xaa Glu Xaa Ile Pro Glu Glu Ala Xaa Xaa
1                  5                        10

(2) INFORMATION FOR SEQ ID NO:8:
    (i) SEQUENCE CHARACTERISTICS:
        (A) LENGTH: 10 amino acids
        (B) TYPE: amino acid
        (D) TOPOLOGY: linear
    (ii) MOLECULE TYPE: peptide
    (ix) FEATURE:
        (A) NAME/KEY: Peptide
        (B) LOCATION: 1..10
        (D) OTHER INFORMATION: /label = Features
            /note = "Serine protease inhibitor; carboxy
            terminus of Hirudin."
    (ix) FEATURE:
        (A) NAME/KEY: Peptide
        (B) LOCATION: 1
        (D) OTHER INFORMATION: /label = Features
            /note = "Xaa = N-alpha-succinyl-tyrosine (Suc—Tyr)"
    (ix) FEATURE:
        (A) NAME/KEY: Peptide
        (B) LOCATION: 3
        (D) OTHER INFORMATION: /label = Features
            /note = "Xaa = L-1,2,3,4-Tetrahydroisoquinoline-3-carboxylate (Tiq)"
    (ix) FEATURE:

SEQUENCE LISTING (A) NAME/KEY: Peptide
                (B) LOCATION: 9
                (D) OTHER INFORMATION: /label = Features
                    /note = "Xaa = Cyclohexylalanine (Cha)"
         (ix) FEATURE:
                (A) NAME/KEY: Peptide
                (B) LOCATION: 10
                (D) OTHER INFORMATION: /label = Features
                    /note = "Xaa = D-glutamic acid (D-Glu)"
         (ix) FEATURE:
                (A) NAME/KEY: Peptide
                (B) LOCATION: 1..10
                (D) OTHER INFORMATION: /label = Properties
                    /note = "Hirudin peptide is a potent
                    thrombin-specific protease inhibitor that forms a
                    stable non-covalent complex with"
         (ix) FEATURE:
                (A) NAME/KEY: Peptide
                (B) LOCATION: 1..10
                (D) OTHER INFORMATION: /label = Properties
                    /note = "(cont'd) alpha-thrombin. Unlike other
                    thrombin inhibitors, said peptide does not occupy
                    the catalytic site of"
         (ix) FEATURE:
                (A) NAME/KEY: Peptide
                (B) LOCATION: 1..10
                (D) OTHER INFORMATION: /label = Properties
                    /note = "(cont'd) alpha-thrombin to inhibit
                    cleavage of fibinogen."
         (xi) SEQUENCE DESCRIPTION: SEQ ID NO:8:

Xaa   Glu   Xaa   Ile   Pro   Glu   Glu   Ala   Xaa   Xaa
1                       5                             10

(2) INFORMATION FOR SEQ ID NO:9:
      (i) SEQUENCE CHARACTERISTICS:
            (A) LENGTH: 10 amino acids
            (B) TYPE: amino acid
            (D) TOPOLOGY: linear
     (ii) MOLECULE TYPE: peptide
     (ix) FEATURE:
            (A) NAME/KEY: Peptide
            (B) LOCATION: 1..10
            (D) OTHER INFORMATION: /label = Features
                /note = "Serine protease inhibitor; carboxy
                terminus of Hirudin"
     (ix) FEATURE:
            (A) NAME/KEY: Peptide
            (B) LOCATION: 1
            (D) OTHER INFORMATION: /label = Features
                /note = "Xaa = N-alpha-succinyl-tyrosine (Suc—Tyr)"
     (ix) FEATURE:
            (A) NAME/KEY: Peptide
            (B) LOCATION: 5
            (D) OTHER INFORMATION: /label = Features
                /note = "Xaa = L-1,2,3,4-Tetrahydroisoquinoline-3-carboxylate (Tiq)"
     (ix) FEATURE:
            (A) NAME/KEY: Peptide
            (B) LOCATION: 9
            (D) OTHER INFORMATION: /label = Features
                /note = "Xaa = Cyclohexylalanine (Cha)"
     (ix) FEATURE:
            (A) NAME/KEY: Peptide
            (B) LOCATION: 10
            (D) OTHER INFORMATION: /label = Features
                /note = "Xaa = D-glutamic acid (D-Glu)"
     (ix) FEATURE:
            (A) NAME/KEY: Peptide
            (B) LOCATION: 1..10
            (D) OTHER INFORMATION: /label = Properties
                /note = "Hirudin peptide is a potent
                thrombin-specific protease inhibitor that forms a
                stable non-covalent complex with"
     (ix) FEATURE:
            (A) NAME/KEY: Peptide
            (B) LOCATION: 1..10
            (D) OTHER INFORMATION: /label = Properties
                /note = "(cont'd) alpha-thrombin. Unlike other
                thrombin inhibitors, said peptide does not occupy
                the catalytic site of"
     (ix) FEATURE:
            (A) NAME/KEY: Peptide

| SEQUENCE LISTING |
|---|
| (B) LOCATION: 1..10<br>(D) OTHER INFORMATION: /label = Properties<br>/note = "(cont'd) alpha-thrombin to inhibit<br>cleavage of fibinogen."<br>(xi) SEQUENCE DESCRIPTION: SEQ ID NO:9:<br>Xaa Glu Pro Ile Xaa Glu Glu Ala Xaa Xaa<br>1                      5                                 10 |

ANTICOAGULANT PEPTIDES

CROSS-REFERENCE TO RELATED APPLICATION

This is a continuation of application Ser. No. 07/645,539, filed Jan. 24, 1991; which is a continuation-in-part application of 07/281,121, filed Dec. 7, 1988, both now abandoned.

FIELD OF INVENTION

This invention relates to novel peptides which are useful anticoagulant agents.

BACKGROUND OF INVENTION

Anticoagulants are useful therapeutic agents in the pharmacological treatment of, for example, acute deep venous thrombosis, pulmonary embolism, acute arterial embolization of the extremities, myocardial infarction, and disseminated intravascular coagulation. Prophylactic administration of anticoagulants is believed to prevent a recurrence of embolism in patients with rheumatic or arteriosclerotic heart disease and to prevent certain thromboembolic complications of surgery. Administration of anticoagulants has also been indicated in the treatment of coronary artery and cerebrovascular disease. Arterial thrombosis, particularly in arteries supplying the heart muscle and brain, is a leading cause of death.

Hirudin is a 65 residue polypeptide isolated from the salivary glands of leeches. It is an anticoagulant agent, which is a thrombin specific inhibitor. Although quite potent, clinical use of hirudin isolated from leech extracts seems unlikely because of its limited quantity, expense and allergic reactions which commonly follow administration of any foreign protein of this size.

Applicants have discovered a specific region of hirudin that is responsible, at least in part, for its anticoagulant activity. This region has been chemically synthesized and certain of its analogs appear to bind to the recognition site of thrombin but not the enzymatic cleavage site which is spatially separate. Binding of the synthetic peptides competitively prevents binding of the fibrinogen to the recognition site of thrombin, a prerequisite to fibrin production and clot formation. The peptides of this invention possess significant anticoagulant activity and their unusual ability to bind only to the recognition site without binding to the cleavage site of thrombin may allow for a scientifically interesting and therapeutically significant adjunct to anticoagulant therapy.

SUMMARY OF THE INVENTION

Peptide derivatives of the formula

X-A$_1$-A$_2$-A$_3$-A$_4$-A$_5$-A$_6$-A$_7$-A$_8$-A$_9$-A$_{10}$-Y wherein

X is an amino terminal residue selected from hydrogen, one or two alkyl groups of from 1 to 6 carbon atoms, one or two acyl groups of from 2 to 10 carbon atoms, carbobenzyloxy or t-butyloxy carbonyl;

A$_1$ is a bond or is a peptide containing from 1 to 11 residues of any amino acid;

A$_2$ is Phe, SubPhe, $\beta$-(2- and 3-thienyl)alanine, $\beta$-pyridyl)alanine, $\beta$-(benzothienyl-2- and 3-yl)alanine, $\beta$-(1- and 2-naphthyl)alanine, Tyr or Trp;

A$_3$ is Glu or Asp;

A$_4$ is any amino acid or a group selected from X1–X23;

A$_5$ is Ile, Val, Leu, Nle, or Phe;

A$_6$ is Pro, Hyp, 3,4-dehydroPro, thiazolidine-4-carboxylate, Sar, NMePgl, D-Ala, or a group selected from X1–X23;

A$_7$ is a bond or any amino acid;

A$_8$ is any amino acid;

A$_9$ is a lipophilic amino acid selected from Tyr, Trp, Phe, Leu, Nle, Ile, Val, Cha and Pro or is a dipeptide containing at least one of these lipophilic amino acids;

A$_{10}$ is a bond or is a peptide fragment containing from one to five residues of any amino acid; and Y is a carboxy terminal residue selected from OH, C$_1$–C$_6$ alkoxy, amino, mono- or di-(C$_1$–C$_4$) alkyl substituted amino, or benzylamino;

X1–X23 are as follows:

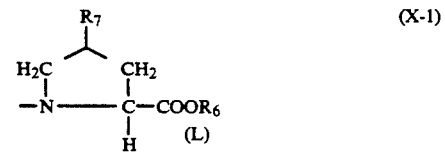

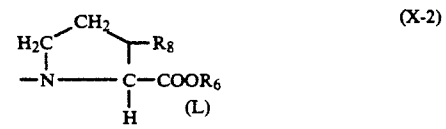

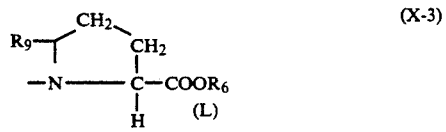

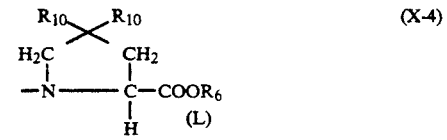

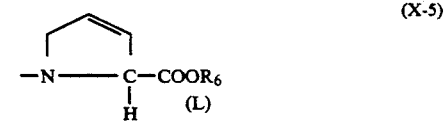

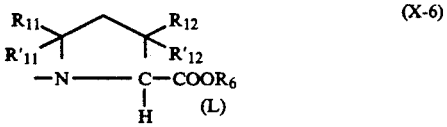

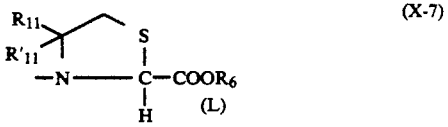

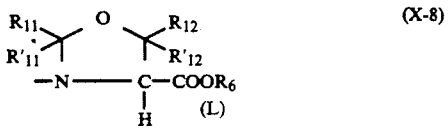

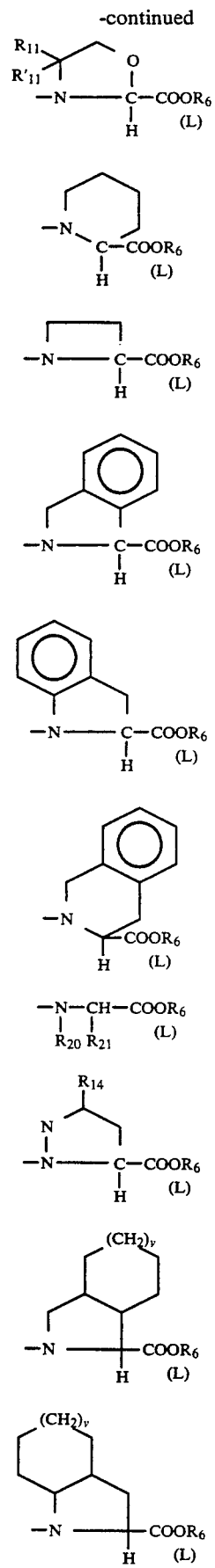

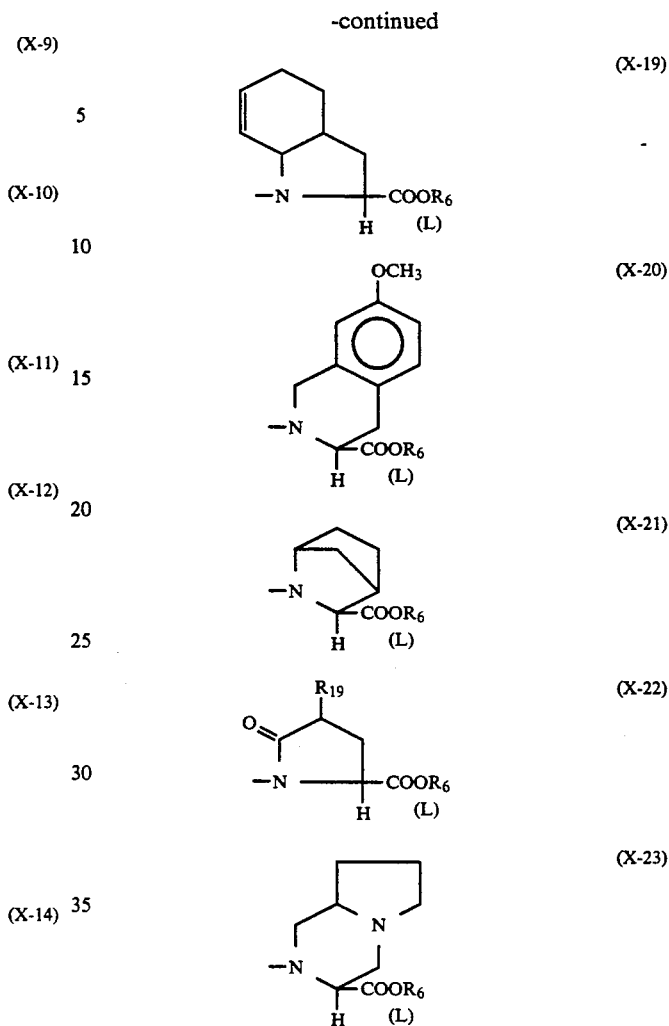

wherein
R$_7$ is H, alkyl, halo, OH, NH—CO—(C$_1$-C$_4$)alkyl, NH$_2$, NR$_{22}$R$_{23}$, NH—CO—(CH$_2$)$_m$Ph, (CH$_2$)$_m$—Y, OCO—N(R$_{15}$)$_2$, O—alkyl, O—(CH$_2$)$_m$—F', (C$_1$-C$_4$)alkylthio or S—(CH$_2$)$_m$—F':

Y is Ph', thienyl, furyl, cycloalkyl, pyridyl, 1- or 2-Nap;

Ph' is phenyl optionally substituted by (R$_{13}$)$_p$—;

Nap is naphthyl optionally substituted by (R$_5$)$_p$—;

F' is Ph' or Nap;

R$_8$ is allyl, halo, —O—CO—N(R$_{15}$)$_2$, —O—(CH$_2$)$_m$—F', (C$_1$-C$_4$)alkoxy, (C$_1$-C$_4$)alkylthio or S—(CH$_2$)$_m$—F';

R$_9$ is (C$_1$-C$_4$)alkyl, keto or —(CH$_2$)$_m$—Ph';

R$_{10}$ is halo or Y'-R$_{16}$;

R$_{11}$, R'$_{11}$, R$_{12}$ and R'$_{12}$ are H or (C$_1$-C$_4$)alkyl; or R'$_{11}$, R$_{12}$ and R'$_{12}$ are H and R$_{11}$ is Ph;

R$_{13}$ is (C$_1$-C$_4$)alkyl, (C$_1$-C$_4$)alkoxy, (C$_1$-C$_4$)alkylthio, Cl, Br, F, CF$_3$, OH, phenyl, phenoxy, phenylthio or phenylmethyl;

R$_5$ is (C$_1$-C$_4$)alkyl, (C$_1$-C$_4$)alkoxy, (C$_1$-C$_4$)alkylthio, Cl, Br, F, CF$_3$ or OH;

m is 0–4;

p is 1–3 provided that p is mor than 1 only if R$_{13}$ or R$_5$ is Me, MeO, Cl, Br or F;

R$_{14}$ is H, (C$_1$-C$_4$)alkyl, Ph, thienyl, furyl or pyridyl;

R$_{15}$ is H or (C$_1$-C$_4$)alkyl;

Y' is O or S;

$R_{16}$ ($C_1$-$C_4$)alkyl or $(CH_2)_m$—Ph'; or the $R_{16}$ groups join to complete a 5- or 6-membered ring in which one or more of the carbon atoms is optionally substituted by ($C_1$-$C_4$)alkyl Or di-(1–4C)alkyl;

$R_{17}$ is H, ($C_1$-$C_4$)alkyl, ($C_4$-$C_8$)cycloalkyl or phenyl;

$R_{18}$ is H, ($C_1$-$C_4$)alkyl, ($C_1$-$C_4$)alkoxy or phenyl:

v is 0-2:

$R_{19}$ is ($C_1$-$C_4$)alkyl or $(CH_2)_r$-phenyl;

$R_{20}$ is H, alkyl, —$(CH_2)_m$—Z (but not when Z is unsubstituted phenyl), indan-2-yl or perhydroindan-2-yl;

$R_{21}$ is H, ($C_1$-$C_4$)alkyl or $(CH_2)_r$-G;

G is phenyl, 4-hydroxy- or 3,4-dihydroxy phenyl, OH, 1H-indol-3-yl, 1H-imidazol-4-yl, $NH_2$, SH, S-alkyl, guanidino or $CONH_2$;

$R_{22}$ is ($C_1$-$C_4$)alkyl, benzyl or phenethyl;

$R_{23}$ is H, ($C_1$-$C_4$)alkyl, benzyl or phenethyl; and $R_6$ is H, ($C_1$-$C_4$)alkyl, benzyl, benzhydryl, alkali or alkaline earth metal salt ion, —CH($R_{1-7}$)—O—$COR_{18}$ or $(CH_2)_2SiMe_3$, with the proviso that one or both of $A_4$ and $A_6$ must be selected from X1-X23 and with the further proviso that $A_4$ and $A_6$ cannot both be a Pro.

DETAILED DESCRIPTION OF THE INVENTION

The following common abbreviations of the amino acids are used throughout this specification:

Gly—glycine
Ala—alanine
Val—valine
Leu—leucine
Ile—isoleucine
Cha—cyclohexylalanine
Orn—ornithine
Pro—proline
Phe—phenylalanine
Trp—tryptophan
Met—methionine
Ser—serine
Thr—threonine
Cys—cysteine
Tyr—tyrosine
Asn—asparagine
Gln—qlutamine
Asp—aspartic acid
Glu—glutaminc acid
Lys—lysine
Arg—arginine
His—histidine
Nle—norleucine
Hyp—hydroxyproline
Glt—glutaryl
Mal—maleyl
Npa—β-(2-naphthyl)alanine
3,4-dehydroPro—3,4-dehydroproline
Tyr($SO_3H$)—tyrosine sulfate
Pgl—phenylglycine
NMePgl—N-methyl-phenylglycine
Sar—sarcocine (N-methylglycine)
pSubPhe—para substituted phenylalanine
SubPhe—ortho, meta, or para, mono- or di- substituted phenylalanine
DAla—D-alanine
Ac—acetyl
Suc—succinyl
pClPhe—para-chloro-phenylalanine
pNO2Phe—para-nitro-phenylalanine
Pip—L-2-pipecolic acid
Azd—L-azetidine-2-carboxylate
Tiq—L-1,2,3,4-tetrahydroisoquinoline-3-carboxylate
Thz—L-thiazolidene-4-carboxylate An alkyl group and the alkyl portion of an alkoxy group is taken to include straight, branched, or cyclic alkyl groups, for example, methyl, ethyl, propyl, isopropyl, butyl, isobutyl, tert-butyl, pentyl, isopentyl, sec-pentyl, cyclopentyl, hexyl, isohexyl, cyclohexyl and cyclopentylmethyl. An acyl group of from 2 to 10 carbon atoms is taken to include straight, branched, cyclic, saturated and unsaturated acyl groups having 1 or 2 carbonyl moieties per group, for example, . A halogen group is a fluoro, chloro, bromo or iodo group.

The term "any amino acid" as used herein includes the naturally occurring amino acids as well as other "non-protein" α-amino acids commonly utilized by those in the peptide chemistry arts when preparing synthetic analogs of naturally occurring peptides. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine. Examples of "non-protein" α-amino acids are norleucine, norvaline, alloisoleucine, homoarginine, thiaproline, dehydroproline, hydroxyproline (Hyp), homoserine, cyclohexylglycine (Chg), α-amino-n-butyric acid (Aba), cyclohexylalanine (Cha), aminophenylbutyric acid (Pba), phenylalanines substituted at the ortho, meta, or para-position of the phenyl moiety with one or two of the following, a ($C_1$-$C_4$) alkyl, ($C_1$-$C_4$) alkoxy, halogen, or nitro groups or substituted with a methylenedioxy group, β-2 and 3-thienylalanine, β-2- and 3-furanylalanine, p-2-, 3-, and 4-pyridylalanine, β-(benzothienyl-2- and 3-yl)alanine, β-(1- and 2-naphthyl)alanine, O-alkylated derivates of serine, threonine, or tyrosine, S-alkylated cysteine, the O-sulfate ester of tyrosine, 3,5-diiodotyrosine and the D-isomers of the naturally occurring amino acids.

The term "lipophilic amino acid" includes Tyr, Phe, Leu, Nle, Ile, Val, His and Pro.

The natural amino acids with the exception of glycine, contain a chiral carbon atom. Unless otherwise specifically indicated, the optically active amino acids, referred to herein, are of the L-configuration. For example, any of the amino acids of the $A_1$ or $A_{10}$ group can be of the D- or L-configuration. As is customary, the structure of peptides written out herein is such that the amino terminal end is on the left side of the chain and the carboxy terminal end is on the right side of the chain.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine.

As with any generic group of chemical compounds, certain groups are preferred. Applicants prefer those peptide derivatives of formula 1 wherein
X is hydrogen, acetyl, or succinyl.

Also preferred are those formula 1 compounds wherein $A_1$ is Thr-Pro-Lys-Pro-Gln-Ser-His-Asn-Asp-Gly-Asp, -Ser-Thr-Pro-Asn-Pro-Glu-Ser-His-Asn-Asn-Gly-Asp-, -His-Asn-Asp-Gly-Asp-, -Asn-Asp-Gly-Asp-, -Asp-Gly-Asp-, -Gly-Asp-, -Asp-, or a bond.

$A_2$ is preferably Phe, β-2- or 3-thienylalanine, Tyr, Trp, Npa or pClPhe;
$A_3$ is Glu;
$A_4$ is Glu, Asp, Pro, Ala, Pip, Azd, Tiq, or Thz;
$A_5$ is Ile, Leu;
$A_6$ is Pro, Sar, D-Ala, Hyp, NMePgl, Pip, Azd, Tiq, or Thz;
$A_7$ is Glu, Gln, Asp or Ala;
$A_8$ is Glu, Asp or Ala;
$A_9$ is Pro, Ala-Tyr, Ala-Cha, Tyr-Cha, Tyr-Leu, Ala-Phe, Tyr-Tyr;
$A_{10}$ is Glu, Asn, Asp-Glu, Pro, Gln, Ala, a bond, D-Lys, Lys, D-Asp or Orn; and
Y is OH or $NH_2$.

Especially preferred are those peptide derivatives of formula 1 wherein either X is acetyl and $A_1$ is Gly-Asp or Asp or X is succinyl and $A_1$ is a bond and wherein
$A_2$ is Phe; β-(2-thienylalanine) or Tyr;
$A_3$ is Glu;
$A_4$ is Glu, Pro, Pip, or Azd;
$A_5$ is Ile;
$A_6$ is Pro, Pip, or Azd;
$A_7$ is Glu;
$A_8$ is Glu or Asp;
$A_9$ is Tyr-Leu, Ala-Tyr, Tyr-Tyr, Ala-Phe, Ala-Cha or Pro;
$A_{10}$ is Gln; Asp; Pro; a bond; D-Asp, D-Lys, D-Glu or -Asp-Glu; and
Y is OH or $NH_2$.

The proteins of this invention can be prepared by a variety of procedures readily known to those skilled in the art. Such procedures include the solid phase sequential and block synthesis, gene cloning and combinations of these techniques. The solid phase sequential procedure can be performed using established automated methods such as by use of an automated peptide sythesizer. In this procedure an α-amino protected amino acid is bound to a resin support. The resin support employed can be any suitable resin conventionally employed in the art for the solid phase preparation of polypeptides, preferably polystyrene which has been cross-linked with from 0.5 to about 3 percent divinyl benzene, which has been either chloromethylated or hydroxymethylated to provide sites for ester formation with the initially introduced α-amino protected amino acid.

An example of a hydroxymethyl resin is described by Bodanszky, et al., Chem. Ind. (London) 38, 1597-98 (1966). A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1–6. The protected amino acid can be bound to the resin by the procedure of Gisin, Helv. Chem Acta, 56, 1476 (1973). Many resin bound, protected amino acids are commercially available. As an example, to prepare a polypeptide of this invention wherein the carboxy terminal end is a Thr residue, a tert-butyloxycarbonyl (Boc) protected Thr bound to a benzylated, hydroxymethylated phenylacetamidomethyl (PAM) resin can be used and is commercially available.

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitro-phenylsulfenyl, tritylsulfenyl, o-nitrophenoxyacetyl and α-chlorobutyryl; (2) aromatic urethan type protecting groups such as benzyloxycarbonyl and substituted benzyloxycarbonyl, such as p-chlorobenzyloxycarbonyl, p-nitrobenzyl- carbonyl, p-bromobenzyloxycarbonyl, p-methoxybenzyloxycarbonyl, 1-(p-biphenylyl)-1-methylethoxycarbonyl, α, α-dimethyl-3,5-dimethoxybenzyloxycarbonyl and benzhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thio urethan type protecting groups such as phenylthiocarbonyl; (6) alkyl type protecting groups such as triphenylmethyl (trityl) and benzyl; and (7) trialkylsilane groups such as trimethylsilane. The preferred α-amino protecting group is tert-butyloxycarbonyl.

The selection of an appropriate coupling reagent is within the skill of the art. A particularly suitable coupling reagent where the amino acid to be added is Gln, Asn or Arg is N,N'-diisopropylcarbodiimide and 1-hydroxy-benzotriazole. The use of these reagents prevents nitrile and lactam formation. Other coupling agents are (1) carbodiimides (e.g., N,N'-dicyclohexylcarbodiimide and N-ethyl-N'-(γ-dimethylaminopropylcarbodiimide); (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyldi-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc) and (8) nitrogen containing heterocyclic compounds having a hydroxy group on one ring nitrogen (e.g., N-hydroxyphthalimide, N-hydroxysuccinimide and 1-hydroxybenzotriazole). Other activating reagents and their use in peptide coupling are described by Kapoor, *J. Pharm. Sci.*, 59, pp. 1-27 (1970). Applicants prefer the use of the symmetrical anhydride as a coupling reagent for all amino acids except Arg, Asn and Gln.

Each protected amino acid or amino acid sequence is introduced into the solid phase reactor in about a fourfold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, *Analyt. Biochem.* 34, 595 (1970).

After the desired amino acid sequence has been obtained, the peptide is removed from the resin. This can be done by hydrolysis such as by treatment of the resin bound polypeptide with a solution of dimethyl sulfide, p-cresol and thiocresol in dilute aqueous hydrofluoric acid.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the α-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxy-carbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

These groups can be removed by procedures well known in the art. Typically protecting group removal is done after the peptide chain synthesis is complete but the protecting groups can be removed at any other appropriate time.

The anticoagulant dose of a peptide derivative of this invention is from 0.2 mg/kg to 250 mg/kg of patient body weight per day depending on the patient, the severity of the thrombotic condition to be treated and the peptide derivative selected. The suitable dose for a particular patient can be readily determined. Preferably from 1 to 4 daily doses would be administered typically with from 5 mg to 100 mg of active compound per dose.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containg a peptide derivative of this invention in a spray or dry powder form.

For parentral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

EXAMPLE 1

Preparation of

Suc-Tyr-Glu-Pro-Ile-Pip-Glu-Glu-Ala-Cha-D-Glu-OH

The peptide was snythesized by solid-phase methods using 0.5 mmol of a 0.56 mmol/g Boc-D-Glu(Bzl)-Merefield resin. Double symmetrical anhydride couplings were performed with 2.0 mmol $N_\alpha$-Boc-amino acid (Peptides International) except in the case of Boc-Pip, which was single coupled. The side chain protection utilized was: Glu(Bzl), Tyr(2-BrZ). The terminal $N_\alpha$-Boc protection was removed with 50% trifluoroacetic acid in methylene chloride. The resin was washed three times with methylene chloride, neutralized with three washings of 10% diisopropylethylamine in methylene chloride, washed three times with methylene chloride. The peptide was end-capped with succinic anhydride (1.0 g) in dimethyl formamide, washed three times with dimethyl formamide, washed three times with methylene chloride, and tested with free amine. The capping reaction was repeated two more times and the resin dried. The peptide was deprotected and cleaved from the resin with HF containing 5% anisole at 0° C., for 45 min. The HF was removed in vacuo at 0° C., the peptide was extracted from the resin with 30% aqueous acetonitrile and lyophilized.

The peptide was purified by preparative HPLC performed on a $C^{18}$ Beckman (50.8×150 mm) column with a 33–38% acetonitrile in 0.1% aqueous TFA at 79 ml/min. The major peak was collected, lyophilized, and further purified on the same column with a 34–35.5% acetonitrile gradient in 0.1% aqueous TFA at 80 ml/min. The major peak was collected and lyophilized to give 104 mg of desired product. Preparative HPLC was performed on a C~Beckman (50.8×150 mm) column with a 33–38% acetonitrile gradient in 0.1% aqueous trifluoroactic acid at 79 ml/min. The major peak was collected and lyophilized leaving 101 mg of the desired produce (58% yield based on initial resin substitution). Homogeneity was determined by HPLC and TLC. HPLC Vydac 218TP54 (250×4.6 mm) $C^{18}$ column, 2 ml/min, $t_o=1.9$ min: time of elution with a 15–40% acetonitrile in 0.1% trifluoroacetic acid linear gradient at 1%/min. (HPLC) is 14.4 min.

Amino acid analysis: (6N HCl hydrolysis; 24 hr. at 106° C.). Glx 4.02 (4); Pro 0.99 (1); Ala 0.99 (1); Ile 0.95 (1); Tyr 0.97(1); Pip 1.08 (1); $\epsilon_{275}=1490$. 91.5 peptide content by weight.

In the same manner, the peptides of the following examples of Anticoagulant peptides were prepared.

ANTICOAGULANT PEPTIDES

PEPTIDE EXAMPLES

EXAMPLE 1

Suc-Tyr-Glu-Pro-Ile-Pip-Glu-Glu-Ala-Cha-D-Glu-OH

EXAMPLE 2

Suc-Tyr-Glu-Pip-Ile-Pro-Glu-Glu-Ala-Cha-D-Glu-OH

EXAMPLE 3

Suc-Tyr-Glu-Pro-Ile-Azd-Glu-Glu-Ala-Cha-D-Glu-OH

EXAMPLE 4

Suc-Tyr-Glu-Azd-Ile-Pro-Glu-Glu-Ala-Cha-D-Glu-OH

EXAMPLE 5

Suc-Tyr-Glu-Tiq-Ile-Pro-Glu-Glu-Ala-Cha-D-Glu-OH

EXAMPLE 6

Suc-Tyr-Glu-Pro-Ile-Tiq-Glu-Glu-Ala-Cha-D-Glu-OH

| PHYSICAL DATA OF COMPOUNDS - AMINO ACID ANALYSIS | | | | | | | |
|---|---|---|---|---|---|---|---|
| | Amino Acids Analysis (6 N HCl Hydrolysis: 24 Hrs at 106° C.) | | | | | | |
| EXAMPLE NO. | Glx | Pro | Ala | Ile | Tyr | Pip | Peptide Content |
| 1 | 4.02 (4) | 0.99 (1) | 0.99 (1) | 0.95 (1) | 0.97 (1) | 1.08 (1) | 91.5% |
| 2 | 3.97 (4) | 1.03 (1) | 0.98 (1) | 0.95 (1) | 0.98 (1) | 1.09 (1) | 84% |
| 3 | 4.04 (4) | 1.03 (1) | 0.98 (1) | 0.97 (1) | 0.98 (1) | | 82% |
| 4 | 4.01 (4) | 1.04 (1) | 0.99 (1) | 0.96 (1) | 1.00 (1) | | 86% |
| 5 | 4.15 | 0.97 | 0.98 | 0.95 | 0.95 | | 77% |
| 6 | 4.12 | 0.99 | 0.98 | 0.95 | 0.98 | | 74% |

| PHYSICAL DATA OF COMPOUNDS - PHYSICAL CHARACTERISTICS | | | BIOLOGICAL DATA FIBRIN CLOT |
|---|---|---|---|
| Physical Characteristics | | | |
| EXAMPLE NO. | HPLC $t_r$ (min) 15–40% gradient) $t_o = 1.65$ min | FAB-MS $(M + H)^+$ | Extinction Coefficient | INHIBITION ASSAY Fibrin Clot Inhibition Inhibition |
| 1 | 14.40 | — | $\epsilon_{275} = 1490$ | 0.88 |
| 2 | 19.05 | 1344 | $\epsilon_{275} = 1630$ | 1.9 |
| 3 | 15.65 | 1316 | $\epsilon_{275} = 1610$ | 0.38 |
| 4 | 16.25 | 1316 | $\epsilon_{275} = 1560$ | 0.51 |
| 5 | — | 1391.9 | $\epsilon_{280} = 1090$ | 0.82 |
| 6 | — | 1391.9 | $\epsilon_{280} = 1220$ | 0.63 |

Details found in the specification

Test data were obtained to prove effectiveness in reducing blood coagulation were performed as follows. Human plasma was collected in EDTA (final concentration=0.1%) from a healthy female volunteer who had fasted for 12 hours. The plasma was immediately sterilized by passing it through a 0.2 u filter membrane (Gelman) then aliquoted into 1 ml portions and stored at −20° C. In all assays, unsulfated Nα-acetylhirudin 45-65 was included as a control. A bovine thrombin solution (50 ul; 0.2 pmol; Sigma) was added to the wells of a 96 well microtiter plate (Falcon) containing 50 ul of a solution and a 10 minute incubation at 24° C., 100 ul of 1:10 diluted human plasma in 0.12M sodium chloride, 0.01M sodium phosphate, 0.01% sodium azide, 0.1% bovine serum albumin (pH 7.4) was added. The mixture was agitated for 20 seconds and the turbidity ($A_{405}$) of the solution was measured at 5 minute intervals by an autoreader (Bio-Tek Model EL 309). Reported is the ability of a 5 uM concentration of peptide to delay two-fold the amount of fibrin clot present at 15 minutes in the control well.

| Specimen Sequence Listing |
|---|

SEQ ID NO: 1
SEQUENCE TYPE: PROTEIN
SEQUENCE LENGTH: 65 AMINO ACIDS
STRANDEDNESS: NOT APPLICABLE
TOPOLOGY: LINEAR
MOLECULE TYPE: PEPTIDE
ORIGINAL SOURCE
ORGANISM: MEDICINAL LEECH (*HIRUDO MEDICNALIS*);
EUKARYOTA; METAZOA; ANNELIDA; HIRUDINEA.
EXPERIMENTAL REFERENCES: [1] (SEQUENCE); DODT J., MULLER
H.-P., SEEMULLER U., CHANG J.-Y.; FEBS LETT. 165:180-
183(1984). [2] (SEQUENCE); PETERSEN T. E., ROBERTS H. R.,
SCOTTUP-JENSEN L., MAGNUSSON S., BAGDY D.; (IN) PROTIDES OF
THE BIOLOGICAL FLUIDS, PROC. 23RD COLLOQ., PEETERS H., ED.,
PP. 145-149, PERGAMON PRESS, NEW YORK, (1976). [3] (STRUCTURE
BY NMR); FOLKERS P. J. M., CLORE G. M., DRISCOLL P. C., DODT J.,
KOEHLER S.
FEATURES: SERINE PROTEASE INHIBITOR; SULFATATION; MULTIGENE
FAMILY; 3D-STRUCTURE; MODIFIED RESIDUE (RES), RES 63
SULFATATION;.
SEQUENCE 65 AA; 6970 MW; 20445 CN;
PROPERTIES: HIRUDIN IS A POTENT THROMBIN-SPECIFIC PROTEASE
INHIBITOR. IT FORMS A STABLE NON-COVALENT COMPLEX WITH
ALPHA-THROMBIN, THEREBY ABOLISHING ITS ABILITY TO CLEAVE
FIBRINOGEN.
SEQUENCE:

| Val | Val | Tyr | Thr | Asp | Cys | Thr | Glu | Ser | Gly | Gln | Asn | Leu | Cyc | Leu |
|---|---|---|---|---|---|---|---|---|---|---|---|---|---|---|
| 1 | | | | 5 | | | | | 10 | | | | | 15 |

| Cys | Glu | Gly | Ser | Asn | Val | Cys | Gly | Gln | Gly | Asn | Lys | Cys | Ile | Leu |
|---|---|---|---|---|---|---|---|---|---|---|---|---|---|---|
| | | | | 20 | | | | | 25 | | | | | 30 |

| Gly | Ser | Asp | Gly | Glu | Lys | Asn | Gln | Cys | Val | Thr | Gly | Glu | Gly | Thr |
|---|---|---|---|---|---|---|---|---|---|---|---|---|---|---|
| | | | | 35 | | | | | 40 | | | | | 45 |

| Pro | Lys | Pro | Gln | Ser | His | Asn | Asp | Gly | Asp | Phe | Glu | Glu | Ile | Pro |
|---|---|---|---|---|---|---|---|---|---|---|---|---|---|---|
| | | | | 50 | | | | | 55 | | | | | 60 |

| Glu | Glu | Tyr | Leu | Gln |
|---|---|---|---|---|
| | | | | 65 |

SEQ ID NO: 2
SEQUENCE TYPE: PROTEIN
SEQUENCE LENGTH: 66 AMINO ACIDS
STRANDEDNESS: NOT APPLICABLE
TOPOLOGY: LINEAR
MOLECULE TYPE: PEPTIDE
ORIGINAL SOURCE
ORGANISM: MEDICINAL LEECH (*HIRUDO MEDICNALIS*);
EUKARYOTA; METAZOA; ANNELIDA; HIRUDINEA.
REFERENCES: [1] (SEQUENCE): DODT J., MACHLEIDT W.,
SEEMULLER U., MASCHLER R., FRITZ H.; BIOL. CHEM. HOPPE-
SEYLER 367:803-811(1986).
FEATURES: SERINE PROTEASE INHIBITOR; MULTIGENE FAMILY;
MODIFIED RESIDUE (RES), RES 64 SULFATATION;. SEQUENCE 66
AA; 7026 MW; 20620 CN.
PROPERTIES: HIRUDIN IS A POTENT THROMBIN-SPECIFIC PROTEASE
INHIBITOR. IT FORMS A STABLE NON-COVALENT COMPLEX WITH
ALPHA-THROMBIN, THEREBY ABOLISHING ITS ABILITIY TO CLEAVE
FIBRINOGEN.
SEQUENCE:

| Ile | Thr | Tyr | Thr | Asp | Cys | Thr | Glu | Ser | Gly | Gln | Asn | Leu | Cys | Leu |
|---|---|---|---|---|---|---|---|---|---|---|---|---|---|---|
| 1 | | | | 5 | | | | | 10 | | | | | 15 |

| Cys | Glu | Gly | Ser | Asn | Val | Cys | Gly | Lys | Gly | Asn | Lys | Cys | Ile | Leu |
|---|---|---|---|---|---|---|---|---|---|---|---|---|---|---|
| | | | | 20 | | | | | 25 | | | | | 30 |

| Gly | Ser | Gln | Gly | Lys | Asp | Asn | Gln | Cys | Val | Thr | Gly | Glu | Gly | Thr |
|---|---|---|---|---|---|---|---|---|---|---|---|---|---|---|
| | | | | 35 | | | | | 40 | | | | | 45 |

| Pro | Lys | Pro | Gln | Ser | His | Asn | Gln | Gly | Asp | Phe | Glu | Pro | Ile | Pro |
|---|---|---|---|---|---|---|---|---|---|---|---|---|---|---|
| | | | | 50 | | | | | 55 | | | | | 60 |

| Glu | Asp | Ala | Tyr | Asp | Glu |
|---|---|---|---|---|---|
| | | | | | 66 |

SEQ ID NO: 3
SEQUENCE TYPE: PROTEIN
SEQUENCE LENGTH: 72 AMINO ACIDS
STRANDEDNESS: NOT APPLICABLE
TOPOLOGY: LINEAR

MOLECULE TYPE: PEPTIDE
ORIGINAL SOURCE
ORGANISM: MEDICINAL LEECH (*HIRUDO MEDICNALIS*);
EUKARYOTA; METAZOA; ANNELIDA; HIRUDINEA.
REFERENCES: [1] (SEQUENCE FROM N.A.); HARVEY R. P., DEGRYSE
E., STEFANI L., SCHAMBER F., CAZENAVE J.-P.,; COURTNEY M.,
TOLSTOSHEV P., LECOCQ J.-P.; PROC. NATL. ACAD. SCI. U.S.A.
83:1084–1088(1986).
FEATURES: SERINE PROTEASE INHIBITOR; SULFATATION; MULTIGENE
FAMILY; SIGNAL SEQUENCE, (−7)–(−1); MATURE HIRUDIN 1–65;
MODIFIED RESIDUE (RES), RES 63 SULFATATION; SEQUENCE 72 AA;
7571 MW; 24730 CN;
PROPERTIES: HIRUDIN IS A POTENT THROMBIN-SPECIFIC PROTEASE
INHIBITOR. IT FORMS A STABLE NON-COVALENT COMPLEX WITH
ALPHA-THROMBIN, THEREBY ABOLISHING ITS ABILITIY TO CLEAVE
FIBRINOGEN.
SEQUENCE:

| Ala −7 | Ile | Cys −5 | Val | Ser | Gln | Ala | Ile 1 | Thr | Tyr | Thr | Asp 5 | Cys | Thr | Glu |
|---|---|---|---|---|---|---|---|---|---|---|---|---|---|---|
| Ser | Gly 10 | Gln | Asn | Leu | Cys | Leu 15 | Cys | Glu | Gly | Ser | Asn 20 | Val | Cys | Gly |
| Lys | Gly 25 | Asn | Lys | Cys | Ile | Leu 30 | Gly | Ser | Asn | Gly | Lys 35 | Gly | Asn | Gln |
| Cys | Val 40 | Thr | Gly | Glu | Gly | Thr 45 | Pro | Asn | Pro | Glu | Ser 50 | His | Asn | Asn |
| Gly | Asp 55 | Phe | Glu | Glu | Ile | Pro 60 | Glu | Glu | Tyr | Leu | Gln 65 | | | |

SEQ ID NO: 4
SEQUENCE TYPE: PROTEIN
SEQUENCE LENGTH: 10 AMINO ACIDS
STRANDEDNESS: NOT APPLICABLE
TOPOLOGY: LINEAR
MOLECULE TYPE: PEPTIDE
ORIGINAL SOURCE: PEPTIDE SYNTHESIS
ORGANISM: NOT APPLICABLE (BASED ON MEDICINAL LEECH *HIRUDO MEDICNALIS*; EUKARYOTA; METAZOA; ANNELIDA; HIRUDINEA).
REFERENCE: SEQUENCE FROM APPLICANTS.
FEATURES: SERINE PROTEASE INHIBITOR; CARBOXY TERMINUS OF
HIRUDIN; MODIFIED RESIDUE (RES), RES 1 SUCCINYLATION (Suc),
RES 5 L-2-PIPECOLIC ACID (Pip), RES 9 CYCLOHEXYLALANE
(Cha), RES 10 D-GLUTAMIC ACID (D-Glu); SEQUENCE 10 AA;
PROPERTIES: HIRUDIN PEPTIDE IS A POTENT THROMBIN-SPECIFIC
PROTEASE INHIBITOR. IT FORMS A STABLE NON-COVALENT COMPLEX,
NOT OCCUPPYING THE CATALYTIC SITE, WITH ALPHA-THROMBIN,
THEREBY ABOLISHING ITS ABILITIY TO CLEAVE FIBRINOGEN.
SEQUENCE:
```
      1                   5                      10
Suc—Tyr—Gly—Pro—Ile—Pip—Glu—Glu—Ala—Cha—D—Glu
```

SEQ ID NO: 5
SEQUENCE TYPE: PROTEIN
SEQUENCE LENGTH: 10 AMINO ACIDS
STRANDEDNESS: NOT APPLICABLE
TOPOLOGY: LINEAR
MOLECULE TYPE: PEPTIDE
ORIGINAL SOURCE: PEPTIDE SYNTHESIS
ORGANISM: NOT APPLICABLE (BASED ON MEDICINAL LEECH *HIRUDO MEDICNALIS*; EUKARYOTA; METAZOA; ANNELIDA; HIRUDINEA).
REFERENCE: SEQUENCE FROM APPLICANTS.
FEATURES: SERINE PROTEASE INHIBITOR; CARBOXY TERMINUS OF
HIRUDIN; MODIFIED RESIDUE (RES), RES 1 SUCCINYLATION (Suc),
RES 3 L-2-PIPECOLIC ACID (Pip), RES 9 CYCLOHEXYLALANINE
(CHA), RES 10 D-GLUTAMIC ACID (D-Glu); SEQUENCE 10 AA;.
PROPERTIES: HIRUDIN PEPTIDE IS A POTENT THROMBIN-SPECIFIC
PROTEASE INHIBITOR. IT FORMS A STABLE NON-COVALENT COMPLEX,
NOT OCCUPPYING THE CATALYTIC SITE, WITH ALPHA-THROMBIN,
THEREBY ABLOISHING ITS ABILITIY TO CLEAVE FIBRINOGEN.
SEQUENCE:
```
      1                   5                      10
Suc—Tyr—Glu—Pip—Ile—Pro—Glu—Glu—Ala—Cha—D—Glu
```

SEQ ID NO: 6
SEQUENCE TYPE: PROTEIN
SEQUENCE LENGTH: 10 AMINO ACIDS
STRANDEDNESS: NOT APPLICABLE
TOPOLOGY: LINEAR

| -continued |
|---|
| Specimen Sequence Listing |

MOLECULE TYPE: PEPTIDE
ORIGINAL SOURCE: PEPTIDE SYNTHESIS.
ORGANISM: NOT APPLICABLE (BASED ON MEDICINAL LEECH *HIRUDO MEDICNALIS*; EUKARYOTA; METAZOA; ANNELIDA; HIRUDINEA).
REFERENCE: SEQUENCE FROM APPLICANTS.
FEATURES: SERINE PROTEASE INHIBITOR; CARBOXY TERMINUS OF HIRUDIN; MODIFIED RESIDUE (RES), RES 1 SUCCINYLATION (Suc), RES 5 L-AZETIDINE-2-CARBOXYLATE (Azd), RES 9 CYCLOHEXYLALANINE (CHA), RES 10 D-GLUTAMIC ACID (D-Glu); SEQUENCE 10 AA.
PROPERTIES: HIRUDIN PEPTIDE IS A POTENT THROMBIN-SPECIFIC PROTEASE INHIBITOR. IT FORMS A STABLE NON-COVALENT COMPLEX, NOT OCCUPPYING THE CATALYTIC SITE, WITH ALPHA-THROMBIN, THEREBY ABOLISHING ITS ABILITIY TO CLEAVE FIBRINOGEN AND NOT OCCUPPY THE CATALYTIC SITE.
SEQUENCE:
  1          5          10
Suc—Tyr—Glu—Pro—Ile—Azd—Glu—Glu—Ala—Cha—D—Glu

SEQ ID NO: 7
SEQUENCE TYPE: PROTEIN
SEQUENCE LENGTH: 10 AMINO ACIDS
STRANDEDNESS: NOT APPLICABLE
TOPOLOGY: LINEAR
MOLECULE TYPE: PEPTIDE
ORIGINAL SOURCE: PEPTIDE SYNTHESIS.
ORGANISM: NOT APPLICABLE (BASED ON MEDICINAL LEECH *HIRUDO MEDICNALIS*; EUKARYOTA; METAZOA; ANNELIDA; HIRUDINEA).
REFERENCE: SEQUENCE FROM APPLICANTS.
FEATURES: SERINE PROTEASE INHIBITOR; CARBOXY TERMINUS OF HIRUDIN; MODIFIED RESIDUE (RES), RES 1 SUCCINYLATION (Suc), RES 3 L-AZETIDINE-2-CARBOXYLATE (Azd), RES 9 CYCLOHEXYLALANINE (CHA), RES 10 D-GLUTAMIC ACID (D-Glu); SEQUENCE 10 AA.
PROPERTIES: HIRUDIN PEPTIDE IS A POTENT THROMBIN-SPECIFIC PROTEASE INHIBITOR. IT FORMS A STABLE NON-COVALENT COMPLEX, NOT OCCUPPYING THE CATALYTIC SITE, WITH ALPHA-THROMBIN, THEREBY ABOLISHING ITS ABILITIY TO CLEAVE FIBRINOGEN AND NOT OCCUPPY THE CATALYTIC SITE.
SEQUENCE:
  1          5          10
Suc—Tyr—Glu—Azd—Ile—Pro—Glu—Glu—Ala—Cha—D—Glu

SEQ ID NO: 8
SEQUENCE TYPE: PROTEIN
SEQUENCE LENGTH: 10 AMINO ACIDS
STRANDEDNESS: NOT APPLICABLE
TOPOLOGY: LINEAR
MOLECULE TYPE: PEPTIDE
ORIGINAL SOURCE: PEPTIDE SYNTHESIS.
ORGANISM: NOT APPLICABLE (BASED ON MEDICINAL LEECH *HIRUDO MEDICNALIS*; EUKARYOTA; METAZOA; ANNELIDA; HIRUDINEA).
REFERENCE: SEQUENCE FROM APPLICANTS.
FEATURES: SERINE PROTEASE INHIBITOR; CARBOXY TERMINUS OF HIRUDIN; MODIFIED RESIDUE (RES), RES 1 SUCCINYLATION (Suc), RES 3 L-1,2,3,4-TETRAHYDROISOQUINOLINE-3-CARBOXYLATE (Tiq), RES 9 CYCLOHEXYLALANINE (CHA), RES 10 D-GLUTAMIC ACID (D-Glu); SEQUENCE 10 AA.
PROPERTIES: HIRUDIN PEPTIDE IS A POTENT THROMBIN-SPECIFIC PROTEASE INHIBITOR. IT FORMS A STABLE NON-COVALENT COMPLEX, NOT OCCUPPYING THE CATALYTIC SITE, WITH ALPHA-THROMBIN, THEREBY ABOLISHING ITS ABILITIY TO CLEAVE FIBRINOGEN AND NOT OCCUPPY THE CATALYTIC SITE.
SEQUENCE:
  1          5          10
Suc—Tyr—Gly—Tiq—Ile—Pro—Glu—Glu—Ala—Cha—D—Glu

SEQ ID NO: 9
SEQUENCE TYPE: PROTEIN
SEQUENCE LENGTH: 11 AMINO ACIDS
STRANDEDNESS: NOT APPLICABLE
TOPOLOGY: LINEAR
MOLECULE TYPE: PEPTIDE
ORIGINAL SOURCE: PEPTIDE SYNTHESIS.
ORGANISM: NOT APPLICABLE (BASED ON MEDICINAL LEECH *HIRUDO MEDICNALIS*; EUKARYOTA; METAZOA; ANNELIDA; HIRUDINEA).
REFERENCE: SEQUENCE FROM APPLICANTS.
FEATURES: SERINE PROTEASE INHIBITOR; CARBOXY TERMINUS OF HIRUDIN; MODIFIED RESIDUE (RES), RES 1 SUCCINYLATION (Suc), RES 3 L-1,2,3,4-TETRAHYDROISOQUINOLINE-3-CARBOXYLATE (Tiq), RES 9 CYCLOHEXYLALANINE (CHA), RES 10 D-GLUTAMIC ACID (D-

-continued

Specimen Sequence Listing

Glu); SEQUENCE 10 AA.
PROPERTIES: HIRUDIN PEPTIDE IS A POTENT THROMBIN-SPECIFIC
PROTEASE INHIBITOR. IT FORMS A STABLE NON-COVALENT COMPLEX,
NOT OCCUPPYING THE CATALYTIC SITE, WITH ALPHA-THROMBIN,
THEREBY ABOLISHING ITS ABILITIY TO CLEAVE FIBRINOGEN AND
NOT OCCUPPY THE CATALYTIC SITE.
SEQUENCE:

```
       1                    5                        10
Suc—Tyr—Glu—Pro—Ile—Tiq—Glu—Glu—Ala—Cha—D—Glu
```

We claim:

1. A peptide derivative of the formula $$X-A_1-A_2-A_3-A_4-A_5-A_6-A_7-A_8-A_9-A_{10}-Y$$

wherein

X is a hydrogen, one or two alkyl groups selected from the group methyl, ethyl, propyl, isopropyl, butyl, isobutyl, and tert-butyl, or one or two acyl groups selected from the group acetyl, and succinyl;

$A_1$ is a bond;
$A_2$ is Tyr;
$A_3$ is Glu;
$A_4$ is Pro, Pip, Azd, or Tiq;
$A_5$ is Ile;
$A_6$ is Pro, Pip, Azd, or Tiq;
$A_7$ is Glu;
$A_8$ is Glu;
$A_9$ is a dipeptide Ala-Cha;
$A_{10}$ is D-Glu; and
Y is a carboxy terminal residue selected from OH, $(C_1-C_6)$ alkoxy, and amino, with the proviso that $A_4$ and $A_6$ cannot both be a Pro.

2. A peptide derivative of claim 1 wherein X is succinyl.

3. A peptide derivative of claim 1 wherein Y is OH.

4. A peptide derivative of claim 1 which is Suc-Tyr-Glu-Pro-Ile-Pip-Glu-Glu-Ala-Cha-D-Glu-OH (SEQ ID NO. 4).

5. A peptide derivative of claim 1 which is Suc-Tyr-Glu-Pip-Ile-Pro-Glu-Glu-Ala-Cha-D-Glu-OH (SEQ ID NO. 5).

6. A peptide derivative of claim 1 which is Suc-Tyr-Glu-Pro-Ile-Azd-Glu-Glu-Ala-Cha-D-Glu-OH (SEQ ID NO. 6).

7. A peptide derivative of claim 1 which is Suc-Tyr-Glu-Azd-Ile-Pro-Glu-Glu-Ala-Cha-D-Glu-OH (SEQ ID NO. 7).

8. A peptide derivative of claim 1 which is Suc-Tyr-Glu-Tiq-Ile-Pro-Glu-Glu-Ala-Cha-D-Glu-OH (SEQ ID NO. 8).

9. A peptide derivative of claim 1 which is Suc-Tyr-Glu-Pro-Ile-Tiq-Glu-Glu-Ala-Cha-D-Glu-OH (SEQ ID NO. 9).

10. A method of reducing blood coagulation in a patient in need thereof which comprises administering an anticoagulant effective amount of a peptide derivative of one of claims 1–9.

* * * * *